US008361525B2

(12) United States Patent
Garault et al.

(10) Patent No.: US 8,361,525 B2
(45) Date of Patent: Jan. 29, 2013

(54) CULTURE METHOD FAVORISING THE PRODUCTION OF K2 VITAMIN BY LACTIC BACTERIA AND APPLICATIONS THEREOF IN THE PREPARATION OF FOOD PRODUCTS

(75) Inventors: Peggy Garault, Montlhery (FR); Gaëlle Quere, Villebon sur Yvette (FR); Guillaume Catonnet, Massy (FR); Chantal Lamiche, Verrieres le Buisson (FR); Jean-Michel Faurie, Jouy en Josas (FR)

(73) Assignee: Compagnie Gervais Danone, Paris (FR)

( * ) Notice: Subject to any disclaimer, the term of this patent is extended or adjusted under 35 U.S.C. 154(b) by 595 days.

(21) Appl. No.: 12/444,027

(22) PCT Filed: Oct. 4, 2007

(86) PCT No.: PCT/EP2007/060551
§ 371 (c)(1),
(2), (4) Date: Jun. 24, 2009

(87) PCT Pub. No.: WO2008/040784
PCT Pub. Date: Apr. 10, 2008

(65) Prior Publication Data
US 2010/0047385 A1 Feb. 25, 2010

(30) Foreign Application Priority Data
Oct. 4, 2006 (FR) ...................................... 06 08692

(51) Int. Cl.
*A23L 1/28* (2006.01)
(52) U.S. Cl. ................. 426/7; 426/61; 426/72; 435/133
(58) Field of Classification Search ................. 426/7, 61, 426/72; 435/133
See application file for complete search history.

(56) References Cited

U.S. PATENT DOCUMENTS
2005/0032196 A1* 2/2005 Duwat et al. ............... 435/252.9

FOREIGN PATENT DOCUMENTS
JP 10-056959 * 10/1998
JP 2000-287676 A 10/2000

OTHER PUBLICATIONS

JP-10-056959-1998-Machine Translation.*
Gaudu, P. et al. 2002. Respiration capacity and consequences in *Lactococcus lactis*. Antonie van Leeuwenhoek. 82: 263-269.*
Bolotin et al., "The Complete Genome Sequence of the Lactic Acid Bacterium *Lactococcus lactis* ssp. *lactis* IL 1403", Genome Research, 2001, vol. 11, pp. 731-753, Cold Spring Harbour Laboratory Press.
Booth et al., "Dietary vitamin K intakes are associated with hip fracture but not with bone mineral density in eldery men and women", Am. J. Clin. Nutr., 2000, vol. 71, pp. 1201-1208, American Society for Clinical Nutrition.
Braam et al., "Vitamin K1 Supplementation Retards Bone Loss in Postmenopausal Women Between 50 and 60 Years of Age", Calcified Tissue International, 2003, vol. 73, pp. 21-26.
Cocaign-Bousquet et al., "Rational development of a simple synthetic medium for the sustained growth of *Lactococcus lactis*", Journal of Applied Bacteriology, 1995, vol. 79, pp. 108-116, The Society for Applied Bacteriology.
Demain, "Industrial Microbiology", Science, vol. 214, Nov. 27, 1981, pp. 987-995, XP-002440835.
Ducy et al., "Increased bone formation in osteocalcin-deficient mice", Nature, vol. 382, Aug. 1, 1996, pp. 448-452.
Duwat et al., "Respiration Capacity of the Fermenting Bacterium *Lactococcus lactis* and Its Positive Effects on Growth and Survival", Journal of Bacteriology, Aug. 2001, vol. 183, No. 15, pp. 4509-4516, American Society for Microbiology.
Hart et al., "Circulating Vitamin $K_1$ Levels in Fractured Neck of Femur", The Lancet, Aug. 4, 1984, p. 283.
Hart et al., "Electrochemical Detection of Depressed Circulating Levels of Vitamin $K_1$ in Osteoporosis", Journal of Clinical Endocrinology and Metabolism, 1985, vol. 60, No. 6, pp. 1268-1269, The Endocrine Society.
Hauschka et al., "Osteocalcin and Matrix Gla Protein: Vitamin K-Dependent Proteins in Bone", Physiological Reviews, Jul. 1989, vol. 69, No. 3, pp. 990-1047, The American Physiological Society.
Hirano et al., "Effects of vitamin $K_2$, vitamin D, and calcium on the bone metabolism of rats in the growth phase", Journal of Orthopaedic Science, 2002, vol. 7, pp. 364-369, The Japanese Orthopaedic Association.
Knapen et al., "The Effect of Vitamin K Supplementation on Circulating Osteocalcin (Bone Gla Protein) and Urinary Calcium Excretion", Annals of Internal Medicine, 1989, vol. 111, pp. 1001-1005, American College of Physicians.
Morishita et al., "Production of Menaquinones by Lactic Acid Bacteria", J. Dairy Sci., 1999, vol. 82, pp. 1897-1903.
Parker et al., "Mixed Cultures of Food-grade Probiotic Bacteria and Enteric Bacteria Demonstrate Both Synergism and Inhibition of Menaquinone Production", Journal of Food Science, 2003, vol. 68, No. 7, pp. 2325-2330, Institute of Food Technologies.
Ronden et al., "Tissue distribution of K-vitamers under different nutritional regimens in the rat", Biochimica et Biphysica Acta, 1998, vol. 1379, pp. 16-22, Elsevier Science B.V.

(Continued)

*Primary Examiner* — D Lawrence Tarazano
*Assistant Examiner* — Hamid R Badr
(74) *Attorney, Agent, or Firm* — Birch Stewart Kolasch & Birch, LLP (57) ABSTRACT

The present invention relates to a method for increasing the amount of K2 vitamin obtained by culturing at least one stem of a lactic bacteria that produces K2 vitamin, wherein the culture of said stem is realized in resting-cells conditions so that the amount of K2 vitamin produced by the resting-cells culture is higher by a ratio of at least 1.2 to that obtained by the culture of said stem under standard fermentation conditions. The present invention also relates to the biomass obtained from the culture of a lactic bacteria producing K2 vitamin according to the above method. The invention further relates to a method for producing K2 vitamin, to a method for preparing food products, including fermented products and/or fresh diary products, enriched with K2 vitamin, and to the food products thus obtained.

10 Claims, 3 Drawing Sheets

OTHER PUBLICATIONS

Shiraki et al., "Vitamin $K_2$ (Menatetrenone) Effectively Prevents Fractures and Sustains Lumbar Bone Mineral Density in Osteoporosis", Journal of Bone and Mineral Research, 2000, vol. 15, No. 3, pp. 515-521, American Society for Bone and Mineral Research.

Szulc et al., "Serum Undercarboxylated Osteocalcin Is a Marker of the Risk of Hip Fracture in Elderly Women", Apr. 1993, vol. 91, pp. 1769-1774, The American Society for Clinical Investigation, Inc.

Vaananen et al., "Strong Prediction of Fractures Among the Elderly by the Ratio of Carboxylated and Total Serum Osteocalcin", P-120, 1992.

Vido et al., "Roles of Thioredoxin Reductase during the Aerobic Life of *Lactococcus lactis*", Journal of Bacteriology, Jan. 2005, vol. 187, No. 2, pp. 601-610, American Society for Microbiology.

\* cited by examiner

CULTURE METHOD FAVORISING THE PRODUCTION OF K2 VITAMIN BY LACTIC BACTERIA AND APPLICATIONS THEREOF IN THE PREPARATION OF FOOD PRODUCTS

The present invention relates to the field of food products rich in nutrients, vitamins and/or trace elements in order to improve the content and the qualitative and quantitative balance of nutrient intake in man.

The invention relates more particularly to the means of enriching foods in vitamin K.

More precisely, the present invention relates to a method to increase the quantity of vitamin K2 obtained by cultivating at least one strain of lactic acid bacterium that produces vitamin K2, wherein said strain is cultured under "resting-cell" conditions, in such a way that the quantity of vitamin K2 produced by the resting-cell culture is higher, by a factor at least equal to about 1.2, to that obtained by cultivating said strain under standard fermentation conditions.

Further, the present invention relates to the biomass obtained from a culture of a lactic acid bacterium that produces vitamin K2 in accordance with the method above.

The invention also relates to a method of producing vitamin K2, methods of preparing food products enriched in vitamin K2, in particular fermented products and/or fresh dairy products, as well as to the food products thus obtained.

Vitamin K is a fat-soluble vitamin that exists in two natural forms: vitamin K1 (or phylloquinone) and vitamin K2 (or menaquinone)

Vitamin K1 is synthesised by plants. It is found mainly in green vegetables (leafy vegetables) and soya oil.

Vitamin K1 acts more directly in the blood coagulation process.

Vitamin K2 is produced by bacteria of the intestinal flora. It also appears in small quantities in certain foods following fermentation (cheese, typical Asian products containing fermented soya such as Japanese miso and natto, etc.). Many bacteria are able to synthesise vitamin K2. Thus, in addition to the bacteria of the intestinal flora and, notably, the species *Escherichia coli, Bacillus subtilis* and *Bacteroides* spp., examples include certain species or subspecies of lactic acid bacteria such as *Lactococcus lactis* spp. *lactis, Lactococcus lactis* spp. *cremoris, Leuconostoc lactis, Leuconostoc mesenteroides* and *Propionibacterium* sp. The quantity of vitamin K2 synthesised by these bacteria generally varies from about 29 µg to about 90 µg per litre of fermented milk (Morishita et al., 1999). It is important to stress that measurements of vitamin K2 production are generally taken from cell pellet lyophilisates and the results of these measurements reveal great heterogeneity of production levels according to the strains tested, with some strains producing three times more than others (Morishita et al., 1999; Parker et al., 2003). In terms of biological activity, vitamin K2 is known above all for its action on calcification of soft tissues.

Vitamin K was initially described for its essential role in the process of blood coagulation. Thus, large deficiencies in vitamin K lead to haemorrhages, with abnormal prolongation of coagulation time, and to ecchymoses. It has long been believed that large deficiencies in vitamin K were rather rare in adults, with needs being able to be covered satisfactorily in principle by a varied and balanced diet and via endogenous production of the vitamin by colon bacteria. In this respect, people at risk are typically:

newborns, whose intestines at birth do not have the bacteria that produce vitamin K;

people whose hepatic, biliary or intestinal functions are disrupted (hepatic disease, cystic fibrosis, colitis, dysentery, etc.); and, those who take long-term antibiotics.

More recently, it was discovered that the impact of vitamin K on human health was not limited to its role in blood coagulation mechanisms. Indeed, since the 1980's, vitamin K also has been recognised for its role in bone metabolism (Hart et al., 1984; Hart et al., 1985).

This vitamin plays the role of cofactor in an enzymatic reaction that conditions the activity of osteocalcin in the context of regulation of bone formation (Hauschka P V et al., 1989; Ducy P et al., 1996). Its role more precisely consists in conditioning the carboxylation of osteocalcin, a key protein that regulates the process of bone formation. In the event of vitamin K deficiency, this reaction does not take place, leading to an increase in the ratio of decarboxylated osteocalcin to carboxylated osteocalcin in the blood (Väänänen et al., 1999).

Demographic trends in Western countries are resulting in a progressive ageing of the population, associated consequentially with an increase in the prevalence of degenerative pathologies, in particular osteoporosis. For this reason, osteoporosis is now recognised as a major public health problem.

Demographic projections made in the 1990's sounded the alarm by foreseeing a considerable increase in the incidence of this pathology in the next 50 years, notably amongst the elderly. Thus were quickly established the need and the urgency to undertake actions in order to prevent this pathology, up to then screened rarely and treated late.

It is now recognised that prevention of osteoporosis must begin in childhood, through optimal bone growth, and continue throughout life by maintaining bone mass. It is known that nutritional factors play an important role in the development and the maintenance of healthy bone. Until now, the nutritional strategies envisaged or proposed to prevent osteoporosis rest primarily on two key factors, namely calcium and vitamin D. Yet, today it is known that other nutritional factors may be of notable importance.

Due to its major role in bone formation, vitamin K appears more and more in the literature like a promising avenue to preserve bone health in man throughout his life.

The recommended nutritional intake of vitamin K in man (1.5 µg/d/kg weight) was established by taking into account only its role in coagulation. However, recent studies suggest that this recommended nutritional intake is underestimated if the activity of vitamin K in bone metabolism is also taken into account (Ronden et al., 1998).

Even if vitamin K needs remain poorly understood, it remains true that low intake is associated with low bone mass and with increased risk of fractures in adults (Hart et al., 1985; Knapen et al., 1989; Szulc et al., 1993; Booth et al., 2000). Moreover, intervention studies amongst menopausal women showed that vitamin K decreased bone loss in this target group (Shiraki et al., 2000; Braam et al., 2003). Lastly, animal studies suggest that it may play a favourable role in developing peak bone mass, and that this effect is even greater when it is synergistically associated with vitamin D. However, the studies to date that clearly connect vitamin K and bone growth have been undertaken only in animals.

Moreover, recent studies have provided additional arguments in favour of the impact of vitamin K on bone metabolism and, in particular, on the constitution and the preservation of bone mass (Booth et al., 2000; Shiraki et al., 2000; Braam et al., 2003; Hirano and Ishi, 2002).

In contrast with effects on adults, little data is available with regard to the beneficial effects of vitamin K on bone metabolism in children. It is only known that it is essential to optimise bone mass during the period of growth, in order to constitute a maximum bone reserve and to protect the adult against the risk of osteoporosis to come.

In any event, it arises from all of the data available to date that improving the vitamin K content of food products is a particularly important and promising avenue to allow an individual to build and maintain good bone constitution.

In this context, there are already industrial products on the food market that contain a notable quantity of vitamin K. Notable examples include certain dairy products containing lactic acid bacteria, such as "Petits Gervais aux Fruits" marketed in France by the Applicant. Nevertheless, it should be noted that, on the one hand, the vitamin K content of these products generally depends on the type of ferments used and, on the other hand, the strains of *Lactococcus lactis* typically used in dairy products do not produce a sufficient quantity of vitamin K to truly meet the needs of the population or to even help mitigate possible vitamin K deficiencies.

There is thus a need in the state of the art for food products, in particular fermented products and/or fresh dairy products, that contain vitamin K in sufficient quantities to help satisfy the needs of, and if necessary to make up the deficiencies of, children and adolescents as well as adults and the elderly.

Hereafter, the terms "vitamin K2" and "vitamin K" are used indifferently to indicate vitamin K2.

The present invention thus aims at responding to this need by proposing for the first time to prepare food products, such as fermented products and/or fresh dairy products, wherein ferments able to produce vitamin K are implemented under conditions that favour in a quite appreciable manner the production of vitamin K compared to traditional production conditions.

Moreover, in the course of their work, the Inventors obtained novel natural variants of natural strains of lactic acid bacteria which produce quantities of vitamin K that are significantly higher than those produced by the natural strains from which they derive (see the "Examples" section below). Thus, these variants that overproduce vitamin K advantageously can be used under implementation conditions particularly favourable to the production of the inventive vitamin K.

According to a first aspect, the present invention relates to a method to increase the quantity of vitamin K2 obtained by cultivating at least one strain of lactic acid bacterium that produces vitamin K2, wherein said strain is cultured under resting-cell conditions, said method comprising at least:

a) inoculation of a suitable culture medium with a quantity of living bacterial cells ranging from about $10^8$ CFU/ml to about $10^{11}$ CFU/ml; and, b) fermentation of the medium thus inoculated for a period ranging from about 4 hours to about 48 hours, preferably ranging from about 8 hours to about 48 hours, at a temperature ranging from about 4° C. to about 50° C., preferably ranging from about 4° C. to about 40° C., in such a way that at the end of step b) the quantity of vitamin K2 produced by the resting-cell culture is higher, by a factor at least equal to about 1.2, than that obtained by cultivating said strain under standard fermentation conditions.

The expressions "resting-cell culture" and "culture under resting-cell conditions" are part of the common language of the technical field of the present invention. The concept of "resting cells" is thus perfectly clear for the person skilled in the art. In France, these English expressions are well-known and generally are not translated into French.

"Standard fermentation conditions" are, as their name indicates, quite standard and are well known to the person skilled in the art (they are also referred to as "laboratory conditions"). The preferred "standard fermentation conditions" in the context of the present invention are as follows: the strain is pre-cultured on commercial M17 medium (Difco™ M17 agar) or on an equivalent medium, supplemented with 20 µl/ml of 0.5 mg/ml haemin solution in 0.1 M soda. For the following culture, inoculation is carried out at 1% using the pre-culture. Incubation temperature is about 30° C. Aeration is ensured by simple agitation. The fermentation conditions may be modified as needed by the person skilled in the art on the basis of his general knowledge and, perhaps, after experiments to refine the protocol. However, care must be taken to systematically preserve the following three essential criteria: (i) the culture medium is a medium suitable to cultivate strains of lactic acid bacteria, in particular strains of *Lactococcus* spp.; (ii) at least one compound containing a haem core (for example, haemin, catalase or chlorophyll derivatives) is added in the pre-culture medium and/or culture medium (preferably in both the pre-culture medium and the culture medium); and (iii) pre-culture and/or culture (preferably, pre-culture only) is implemented under agitation.

Particular embodiments of the inventive method are such as:

in step a), the culture medium is inoculated with a quantity of living bacterial cells ranging from about $5 \times 10^8$ CFU/ml to about $10^{10}$ CFU/ml, more particularly ranging from about $2 \times 10^9$ CFU/ml to about $6 \times 10^9$ CFU/ml;

in step b), fermentation of the medium is carried out under standard conditions for a period ranging from about 12 hours to about 36 hours, preferentially from about 15 hours to about 24 hours;

in step b), fermentation of the medium is carried out under standard conditions at a temperature ranging from about 15° C. to about 35° C., preferably from about 20° C. to about 30° C.

Preferably, at the end of step b), the quantity of vitamin K2 produced by the resting-cell culture is higher, by a factor at least equal to about 1.5, than that obtained by cultivating said strain under standard fermentation conditions. This factor is more preferably at least equal to about 1.7, more preferably still at least equal to about 1.8, and more preferably still at least equal to about 1.9. Even more preferred values of this factor are about 2, about 2.2, about 2.4, about 2.5, about 2.7, about 2.8, about 2.9, and about 3.

Preferably, using the inventive means, the levels of vitamin K2 production sought are about 30 µg of vitamin K2 per 100 g of fermented milk under standard fermentation conditions. Better yet, production levels can reach about 40 µg of vitamin K2 per 100 g of fermented milk, and, even more preferably, they can be around, or even exceed, about 45 µg or 50 µg of vitamin K2 per 100 g of fermented milk. Thus, production levels of about 55 µg, about 60 µg, about 65 µg, about 70 µg, or about 75 µg of vitamin K2 per 100 g of fermented milk, or even more, are preferred in particular.

According to one embodiment, the strain of lactic acid bacterium that produces vitamin K2, implemented in the context of the inventive method, is selected from the genera *Lactococcus, Leuconostoc, Enterococcus* and *Propionibacterium*. In particular, the strain of lactic acid bacterium used is selected from the species *Lactococcus lactis, Leuconostoc lactis, Leuconostoc pseudomesenteroides, Leuconostoc mesenteroides, Leuconostoc dextranicum, Enterococcus faecium,* and *Propionibacterium* sp. Advantageously, the strain of lactic acid bacterium is selected from the natural variants of *Lactococcus lactis* subsp. *cremoris* that produce vitamin K2 which were obtained by the Inventors in the context of the work reported in the Examples below: variant I-3557 filed with France's *Collection Nationale de Culture des Microorganismes* (CNCM, Pasteur Institute, 25, rue du Docteur Roux, 75724 Paris cedex 15, France) on Jan. 20, 2006, variant I-3558 filed with the CNCM on Jan. 20, 2006 and variant I-3626 filed with the CNCM on Jun. 19, 2006.

Herein, the term "variant" encompasses:
natural variants, i.e., those obtained spontaneously from a reference strain of lactic acid bacterium under the effect of selection pressure; natural variants thus do not undergo any genetic engineering, but are obtained principally by mutation and selection from the reference strain; and,
mutants comprising one or more mutations in their genome, which were induced by genetic engineering, i.e., by techniques of directed mutagenesis, in particular by genetic transformation using vectors, applied to the reference strain.

In all cases, the "variants" are, in the context of the invention, strains able to produce vitamin K2. Advantageously, if the level of production is at least about 5.5 µg of vitamin K2 per 100 g of fermented milk under standard fermentation conditions (also called "laboratory conditions"), the variant can be considered to "overproduce" vitamin K2.

It should be noted that in certain countries, (in particular in Europe) precautions must be taken by food manufacturers when they develop products intended for human and/or animal consumption in which microorganisms are incorporated, more particularly living microorganisms. Indeed, genetically modified organisms (microorganisms in this case; referred to as GMOs or mutants) can cause fear and apprehension in consumers. This negative image from which GMOs suffer in certain countries is such that the public tends to boycott foods containing GMOs. Also, in the context of consumers who require more transparency about content levels in food products offered to them and about the origin of the ingredients these products contain, manufacturers can be led to offer products that are quasi-exclusively, even exclusively, GMO-free. In the context of the present invention, it may thus be advantageous that food products manufactured by industry and containing microorganisms are prepared by using exclusively natural strains or natural variants of natural strains.

According to one embodiment, in step a), the suitable culture medium contains fat. It contains preferably at least about 0.5% fat, more preferentially at least about 1.5% fat, more preferentially still at least about 3.5% fat. One such medium can, for example, contain dairy cream or soya milk. It can also be plain milk or milk whose buffering capacity has been increased. Quite clearly, combinations of these various media can also be envisaged. Examples of "milk with increased buffering capacity" include in particular milk supplemented with β-glycerophosphate and/or citrate and/or milk proteins and/or any suitable food ingredient with a buffering capacity.

For example, semi-skimmed milk typically contains about 1.5% fat; whole milk generally contains about 3.5% fat.

In a preferred embodiment, the inventive method further comprises at least one step preliminary to step a) consisting in pre-cultivating the strain under conditions of respiration, in a suitable pre-culture medium containing at least one porphyrin at a final concentration of at least about 0.5 µg/ml. Even more preferred porphyrin concentrations and/or concentration ranges are at least about 1 µg/ml, better yet at least about 5 µg/ml, and better still at least about 10 µg/ml.

Advantageously, the pre-culture is incubated at a temperature ranging from about 4° C. to about 40° C., preferably at a temperature ranging from about 18° C. to about 35° C., with a preferred temperature of about 30° C.

Pre-culture incubation time can vary according to the strains and to other conditions of implementation. It is preferably at least about 8 hours, more preferably at least about 12 hours, and still more preferably at least about 16 hours.

Pre-culture oxygenation can be carried out by agitation or by aeration.

An intermediate step also can be implemented between the preliminary pre-culture step and step a) of the inventive method. This intermediate step consists in concentrating the biomass obtained at the end of pre-culture, for example by centrifugation of the pre-culture followed by the recovery of the bacterial pellet.

It should be noted that, taking into account the applications of the object of the present invention in the food industry, the conditions implemented will be those that are at once (i) applicable and usable on an industrial scale (in terms of feasibility, yield, cost, equipment, etc.), and (ii) suitable to food products (in terms of physical and organoleptic properties of the finished products (taste, odour, texture, appearance, etc.)).

A second aspect of the present invention relates to the enriched biomass obtainable by culture of at least one strain of lactic acid bacterium that produces vitamin K2 under resting-cell conditions in accordance with the method previously described.

In a third aspect of the present invention, the above-mentioned biomass is used to prepare a food product enriched in vitamin K2.

A fourth aspect of the present invention relates to a method to produce vitamin K2, which comprises at least:
a) implementation of the method to increase the quantity of vitamin K2 obtained by cultivating at least one strain of lactic acid bacterium that produces vitamin K2, in accordance with the preceding description; and,
b) recovery of the vitamin K2 thus produced.

According to a fifth aspect, the present invention relates to methods to prepare a food product enriched in vitamin K2, or to enrich a food product in vitamin K2.

According to a first embodiment, one such method comprises at least:
a) producing vitamin K2 according to the method of the fourth aspect of the invention;
b) adding the vitamin K2 thus produced to said food product, or to an intermediate preparation of same; and,
c) obtaining said food product enriched in vitamin K2.

According to a second embodiment, a method to prepare a food product enriched in vitamin K2 comprises at least:
a) culturing at least one strain of lactic acid bacterium that produces vitamin K2 under resting-cell conditions in accordance with the method to increase the quantity of vitamin K2 obtained from a culture of said strain (first aspect of the invention);
b) adding the biomass obtained from the culture of step a) to said food product or to an intermediate preparation of same; and,
c) obtaining said food product enriched in vitamin K2.

Alternatively, it can be envisaged to carry out steps a) and b) above simultaneously:
a) culturing at least one strain of lactic acid bacterium that produces vitamin K2 under resting-cell conditions in accordance with the method to increase the quantity of vitamin K2 obtained from a culture of said strain (first aspect of the invention) in said food product or in an intermediate preparation of same; and,
b) obtaining the food product enriched in vitamin K2.

In this case, the strain or strains notably may be implemented by using concentrates of bacteria pre-cultivated on-site (on the site where the food products are produced), or by using bacteria pre-cultivated by a ferment supplier and then packaged and dispatched to the site or sites where the food products are produced. Suppliers may package the bacteria in a fresh or frozen state; alternatively, the bacteria can be dried or lyophilized. In all cases, the bacteria are added to the dairy mass in a completely conventional manner (as any other known lactic acid ferment). For the following culturing step under conditions favourable to vitamin K2 production, the inventive conditions of implementation are applied.

Still another embodiment of a method to enrich a food product in vitamin K2 comprises at least:
 a) adding the biomass in conformity with the present invention to said food product or to an intermediate preparation of same; and,
 b) obtaining said food product enriched in vitamin K2.

Typically, the biomass is used in the same way as traditional lactic acid ferment.

A sixth aspect of the present invention relates to a food product enriched in vitamin K2 obtainable by the implementation of a method such as described above.

Alternatively, a food product enriched in vitamin K2 according to the present invention contains the biomass described above.

The invention relates to food products for humans and/or animals, with a preference for products intended for human consumption. Advantageously, such a food product enriched in vitamin K2 increases the strength of the bones of the person who consumes it. Preferably, this person is a child.

Preferably, a food product in the context of the invention is selected from fermented products, fermented or unfermented fresh dairy products, fermented or unfermented products containing juice of plant origin (fruits, vegetables, cereals, soya, etc.), and combinations thereof. More preferably, a food product in the context of the invention is a fermented product and/or a fresh dairy product.

In the context of the invention, "fresh dairy products" indicate more particularly fresh and fermented dairy products, ready for human consumption, i.e., fresh and fermented dairy foods. The present application more particularly relates to fermented milk and to yogurt. Said fresh and fermented dairy foods can alternatively be cottage cheese or "petits-suisses".

"Fermented milk" and "yogurt" have the standard definitions used in the dairy industry, i.e., products which are intended for human consumption and which result from the acidifying lactic acid fermentation of a dairy substrate. These products may contain secondary ingredients such as fruits, plants, sugar, etc. Refer, for example, to French Decree no. 88-1203 of 30 Dec. 1988 relating to fermented milk and yogurt, published in the Official Journal of the French Republic on 31 Dec. 1988.

Reference can also be made to the "Codex Alimentarius" (prepared by the Codex Alimentarius Commission under the aegis of the FAO and the WHO, and published by the Information Division of the FAO, available online at http://www.codexalimentarius.net; see more particularly Volume 12 of the Codex Alimentarius "Codex standards for milk and milk products" and the standard "CODEX STAN A-11(a)-1975").

The expression "fermented milk" is thus reserved in the present application for dairy products prepared with a milk substrate which has undergone a treatment at least equivalent to pasteurisation, inoculated with microorganisms belonging to the species characteristic of each product. "Fermented milk" has not undergone any treatment to subtract a constitutive element of the milk substrate implemented and in particular has not undergone draining of the coagulum. Coagulation of "fermented milk" must not be obtained by means other than those resulting from the activity of the microorganisms used.

The term "yogurt" is reserved for fermented milk obtained, according to local and constant uses, by the development of specific thermophilic lactic acid bacteria named *Lactobacillus bulgaricus* and *Streptococcus thermophilus*, which must be found living in the finished product, at a concentration of at least 10 million bacteria per gram of the milk part.

In some countries, regulations authorise the addition of other lactic acid bacteria in the production of yogurt, and notably the additional use of strains of *Bifidobacterium* and/or *Lactobacillus acidophilus* and/or *Lactobacillus casei*. These additional lactic acid strains are intended to confer on the finished product various properties, such as to support the balance of intestinal flora or to modulate the immune system.

In practise, the expression "fermented milk" is thus generally used to indicate fermented milk other than yogurt. Depending on the country, it also can be called, for example, "Kefir", "Kumiss", "Lassi", "Dahi", "Leben", "Filmjôlk", "Villi" or "Acidophilus milk".

As fermented milk, the quantity of free lactic acid contained in the fermented milk substrate should not be lower than 0.6 g per 100 g at the time of sale to the consumer, and the protein content provided by the milk part should not be lower than that of normal milk.

Lastly, the name "cottage cheese" or "petit-suisse" is, in the present application, reserved for cheese which is not refined, not salted, and which has undergone fermentation by lactic acid bacteria only (and no fermentation other than lactic acid fermentation). The dry matter content of cottage cheese can be lowered to 15 g or 10 g per 100 g of cottage cheese, according to whether their fat content is higher than 20 g, or at most equal to 20 g per 100 g of cottage cheese, after complete desiccation. The dry matter content of cottage cheese is between 13% and 20%. The dry matter content of petit-suisse is not lower than 23 g per 100 g of petit-suisse. It is generally between 25% and 30%. Cottage cheeses and petits-suisses are generally called "fresh cheeses", used in a traditional way in the technical field of the present invention.

The following figures illustrate the present invention, although they in no way limit its object or scope.

It is clear that the present invention is not limited only to the description above. Other embodiments and advantages of the invention will arise upon consideration of the examples, which are provided below on a purely illustrative basis.

EXAMPLES

Part A: Obtaining Natural Variants of Natural Strains of Lactic Acid Bacteria Able to Produce Advantageous Quantities of Vitamin K As preliminary remarks, it should be noted that the protocols for obtaining the natural variants described below are applicable to any type of starting strain of lactic acid bacterium. Depending on the starting strains which the person skilled in the art will use, it may be desirable, for primarily practical reasons, to modify some of the experimental conditions developed by the Inventors. In any event, modifications which the person skilled in the art will be likely to make to the procedures below will be minor and will require only simple and routine operations that do not involve any inventive step.

A-I—Obtaining and Using Natural Variants Resistant to Bacitracin

Although exposure to agents such as bacitracin or peroxide is known to enable selection of bacterial strains that have increased resistance to these agents, a link has never been established in the literature between resistance to bacitracin or peroxide and levels of vitamin K2 production by bacteria.

In the context of their work, the Inventors discovered in a completely unexpected way that bacteria were able to develop an original mechanism of resistance to certain agents such as bacitracin or peroxide, involving an increase in vitamin K2 production. The Inventors envisaged using this discovery for purposes of obtaining, by using bacitracin or peroxide, for example, as an agent to select natural variants of strains of lactic acid bacteria (notably *Lactococcus lactis*) able to overproduce vitamin K2.

A-I-1—Protocol for Obtaining Variants Resistant to Bacitracin

Pre-culture was carried out from a crystal of a natural strain of *Lactococcus lactis* in the presence of 2 ml of traditional commercial M17 culture medium (M17 agar, Difco™) supplemented with 5 g/l lactose (hereafter, M17 Lac) and with haemin (20 µl/ml; hereafter, M17 Lac+haemin). Incubation was carried out under agitation at 30° C.

The pre-culture was used to inoculate 2 ml of M17 Lac+ haemin supplemented with bacitracin (4 µg/ml). The inoculation rate was 1%. The culture was then incubated for 48 hours under agitation at 30° C.

Next, 100 µl of this suspension was deposited on M17 Lac agar. A paper disc soaked with 2.5 mg of bacitracin was deposited in the centre of the dish. The agar was incubated for 48 hours at 30° C. Clones close to the paper disc were cultivated in the presence of bacitracin (4 µg/ml) in 2 ml of M17 Lac+haemin. Incubation lasted for 24 hours under agitation at 30° C.

The cells were isolated on M17 Lac agar in the presence of bacitracin (2 µg/ml) after incubation for 48 hours at 30° C. The isolated clones were cultivated in M17 Lac+haemin, and then incubated for 24 hours under agitation at 30° C. This suspension was used to develop the frozen stock.

These experiments enabled the Inventors to select the natural variant *Lactococcus lactis* subsp. *cremoris* I-3557 filed with the CNCM on Jan. 20, 2006.

A-I-2—Protocol for Preparing an Example of a Dairy Product with the "Bacitracin" Variant Pre-culture was carried out from a crystal of the strain in 2 ml of M17 Lac.

The pre-culture was used to inoculate, at 1%, 50 ml of UHT whole milk which was incubated at 30° C. for 24 hours.

Table I below gives the result of the analysis of vitamin K2 expressed in µg Equivalent MK-4/100 g of product, for the bacitracin-resistant variant and the corresponding wild strain.

TABLE 1

| Strain | I-3557 | Wild |
|---|---|---|
| Vitamin K (in µg/100 g 0 | 8.90 | 3.32 |

The bacitracin-resistant variant thus overproduces vitamin K, by a factor 3, compared with the wild starting strain.

A-II—Obtaining and Using Natural Variants Resistant to Peroxide

*Lactococcus lactis* respiration was demonstrated rather recently (Duwat et al., 2001). Sequencing of the genome of a strain of *L. lactis* (IL1403) confirmed the presence of genes coding for the functions necessary to aerobic respiration (Bolotin et al., 2001). *L. lactis* indeed has the men and cytABCD operons coding for proteins necessary to menaquinone synthesis and to cytochrome D biogenesis. This species also has three genes involved in the last steps of haem synthesis (hemH, hemK and hemN, which are required in the oxidation of porphyrin to attach iron to haem), but does not have genes involved in the first steps of this process. However, *L. lactis* is able to perform oxidative phosphorylation in the presence of protoporphyrinogen.

It has also been shown that *L. lactis* respiration can occur in the presence of oxygen and haem in the culture medium. This respiration enables the cells to reach a greater biomass and the final pH observed is higher than that usually obtained. Cultures in the presence of oxygen and/or haem exhibit comparable growth curves during the first approximately 6 or 7 hours of fermentation. After that, glucose consumption decreases in the case of cultures in the presence of oxygen and haem, and lactate production is thus less. This expresses a shift in metabolism which occurs rather late during culture. *L. lactis* respiration thus occurs towards the end of the exponential growth phase (Duwat et al., 2001).

The role of *L. lactis* respiration is not yet known, no more than the role of vitamin K2 in this species with rather fermentative metabolism. The Inventors further noted that vitamin K2 was produced by strains of *L. lactis* whereas respiration was not induced under the conditions tested (no haem in the medium and no agitation allowing good oxygenation of the medium).

In the cytoplasm, proteins have few disulphide bridges compared to extracellular proteins. There is a widespread enzymatic system that limits the number of disulphide bridges. S—S bonds are reduced to HS functions via an enzyme, thioredoxin. This enzyme is regenerated by thioredoxin reductase. Vido et al. (2005) created by genetic engineering an *L. lactis* mutant called trxB1. The trxB1 gene codes for thioredoxin reductase. The study by two-dimensional electrophoresis of proteins synthesised by this mutant showed that it overproduced some of the enzymes of the vitamin K2 synthesis pathway, namely MenB and MenD enzymes.

In view of this data, as well as according to personal observations, the Inventors supposed that one of the possible avenues to improve vitamin K2 production by *L. lactis* could be to induce respiration. Another avenue could be to try to mobilise vitamin K2 to respond to oxidative stress.

The Inventors thus sought to obtain natural variants resistant to oxidative stress.

A-II-1—Protocol for Obtaining Variants Resistant to Oxidative Stress

Peroxide was selected as an example of an oxidising agent that can be used. Of course, other oxidising agents such as hyperchloric ions, iron ions, menadione, paraquat, oxygen, or any other suitable oxidizing compound, could be used under similar conditions.

After pre-culture on M17 Lac medium, the natural starting strains were re-stabbed on the same medium containing increasing concentrations of peroxide (for example, a range from at least about 20 mg/l to at least about 25 mg/l, about 27 mg/l and about 28.5 mg/l). The cultures were incubated at 30° C. After 24 hours, the first test tubes of the concentration range not exhibiting growth were incubated for 24 hours more. Clones were then isolated by depletion on agar media. A clone was selected for a peroxide concentration of 27 mg/l. The Inventors noted that beyond a peroxide concentration of 28.5 mg/l, there was no growth.

These experiments thus enabled the Inventors to select the natural variant *Lactococcus lactis* subsp. *cremoris* I-3558 filed with the CNCM on Jan. 20, 2006.

A-II-2—Protocol for Producing an Example of a Dairy Product with the "Peroxide" Variant The selected clone was grown in whole milk for 24 hours. Samples were then taken and frozen at −80° C. for later analysis of vitamin K.

Table II below indicates the quantity of vitamin K2 produced by the peroxide-resistant variant, compared to the quantity produced by the starting strain (quantities expressed in µg Equivalent MK-4/100 g of fermented milk).

TABLE II

| Strain | Vitamin K (µg/100 g) |
| --- | --- |
| Wild | 2.92 ± 0.45 |
| I-3558 | 5.94 ± 0.76 |

As Table II above shows, the variant produced about twice as much vitamin K2 compared to the corresponding wild strain.

A-III—Obtaining and Using Natural Variants Resistant to Structural Analogues of Aromatic Amino Acids Aromatic amino acids exert negative feedback on their own synthesis pathway, on the level of a step common to the synthesis pathways of vitamin K and folates. When these amino acids are present in the medium, these pathways are not activated. The Inventors thus sought to lift this negative regulation.

A-III-1 Protocol for Obtaining Variants Resistant to Structural Analogues of Aromatic Amino Acids A natural strain of *L. lactis* was spread over a chemically defined agar medium (Cocaign-Bousquet, M., et al., 1995) not containing tryptophan, phenylalanine, or tyrosine. The term "chemically defined medium" is clearly understood by the person skilled in the art. It is a medium containing only simple and clearly defined compounds (for example: vitamin B9, vitamin B12, adenine, tyrosine, etc.), in contrast with a semi-synthetic medium that contains complex compounds (for example: yeast extract, casein hydrolysate, etc.).

A disc of blotting paper was placed in the centre of the Petri dishes and was soaked with 80 µl of a solution containing 50 mM of the following compounds: m-fluorophenylalanine, p-fluorophenylalanine, m-fluorotyrosine and phenylalanine amide. These compounds are structural analogues of aromatic amino acids. The dishes were incubated at 30° C. A growth inhibition zone appeared around the discs. After 48 hours, resistant clones appeared in this zone. These clones were grown on the chemically defined medium not containing aromatic amino acids. The medium was supplemented with a solution containing the structural analogues of these amino acids. The final concentration of each of these compounds was 1 mM.

A-III-2—Protocol for Producing an Example of a Dairy Product with the "Aromatic Amino Acid" Clones The cultures obtained in accordance with section A-III-1 above were used to inoculate 50 ml of M17 Lac medium (1% inoculation rate) supplemented with 1 ml of haemin solution (500 mg/l). The same cultures were used to inoculate a medium not containing haemin, but placed under agitation. A last type of culture was produced. M17 Lac medium was inoculated and placed at 30° C. without agitation. The cultures were placed overnight at 30° C. under agitation (250 rpm). These cultures were then centrifuged for 5 minutes at 6000 g. The supernatant was removed and replaced by 50 ml of whole milk. After 24 hours, the fermented milk was placed at −80° C. while awaiting analysis of vitamin K2 (see section B-VI below).

Experiments analysing vitamin K2 enabled the Inventors to select one of the clones as being a natural variant that overproduces vitamin K2 (see section B-VI below): it is *Lactococcus lactis* subsp. *cremoris* I-3626 natural variant filed with the CNCM on Jun. 19, 2006.

Part B: Development of Conditions to Implement Lactic Acid Bacteria to Favour Vitamin K Production B-I—Influence of Fat in the Medium During analyses of various products, the Inventors noted that the product containing the most vitamin K2 was fermented cream. Moreover, vitamin K2 is highly hydrophobic. The Inventors thus put forth the hypotheses that the presence of fat, or at the very least, a hydrophobic environment, could favour vitamin K2 production.

Fermentations were thus carried out on milk containing various fat concentrations. Pre-cultures were carried out on M17 Lac medium. The milk was inoculated at 1%. Fermentation was maintained at 30° C. for 24 hours. Then, samples were frozen while awaiting subsequent analysis.

Figure 1:
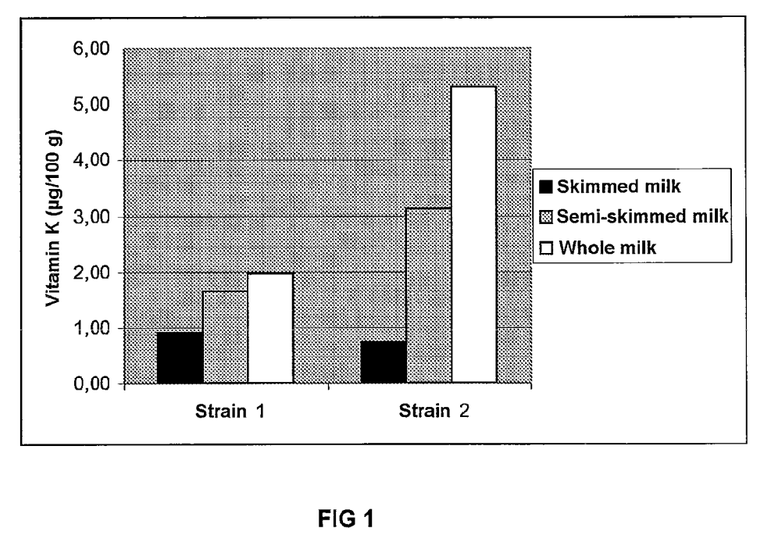
FIG. 1: Histogram illustrating the influence of milk fat concentration on vitamin K2 production by lactic acid bacteria. Strains 1 and 2: examples of natural strains of *Lactococcus lactis* ssp. *cremoris*.

The results are presented in FIG. 1, for two natural strains of *L. lactis* subsp. *cremoris* (strains no. 1 and no. 2).

If the results obtained with one of the two natural strains studied are considered as examples, the use of semi-skimmed milk (about 1.5% fat) instead of skimmed milk increased vitamin K2 production by a factor of 4. Switching from semi-skimmed milk to whole milk (about 3.5% fat) increased production by a factor of 2.

This tendency was the same for all natural strains considered.

However, the increase in the quantity of vitamin K2 produced with that of the fat content of the medium appears asymptotic since fermentation of 40% fat cream did not yield quantities of vitamin K2 higher than those obtained with whole milk (data not shown).

B-II—Influence of Lactic Acid Bacteria Growth Rate

During the growth in milk of a natural strain of *L. lactis* subsp. *cremoris* (natural strain no. 1), the Inventors monitored the kinetics of vitamin K2 production.

Figure 2:
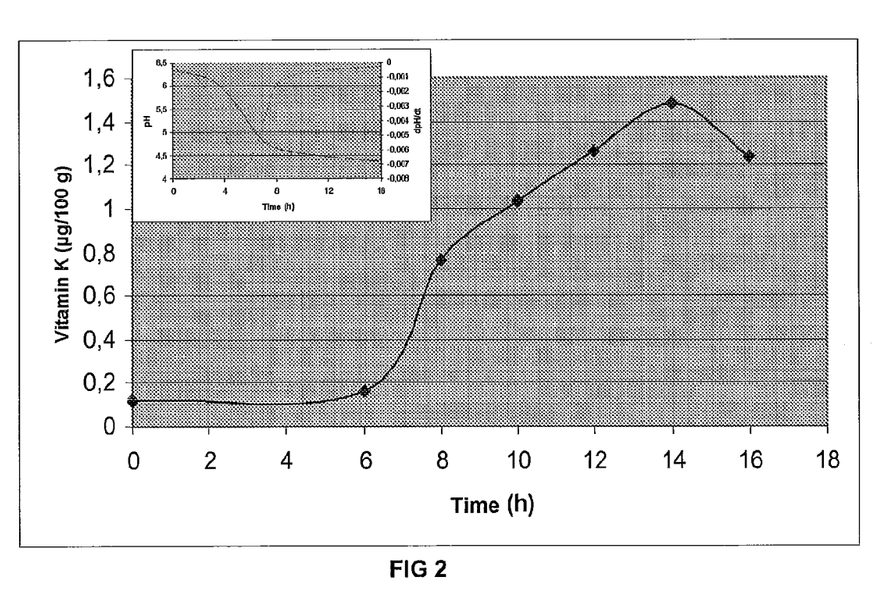
FIG. 2: Examples of vitamin K2 production kinetics in whole milk and acidification kinetics (upper left inset) for a natural strain of lactic acid bacterium (strain no. 1).

As shown in FIG. 2, vitamin production began only when growth slowed. Growth rate could be determined by monitoring acidification kinetics. When the maximum acidification rate was reached, the bacteria entered a slowing phase.

This type of behaviour is relatively standard during the synthesis of secondary metabolites. Various parameters can be studied in order to decrease growth rate: sub-optimal physicochemical conditions (pH, temperature, etc.), bacteriostatic compounds (antibiotics), resting-cell culture. The latter technique consists in performing inoculation with a quantity of cells corresponding at least to that obtained normally at the end of traditional fermentation. In this case, there is no bacterial growth, the growth rate is nil.

The Inventors thus sought to combine resting-cell culture and temperature effect.

Whole milk was inoculated with a direct inoculation ferment containing $10^{11}$ CFU/g at a concentration of 10 g/l. The milk was then incubated at various temperatures.

Figure 3:
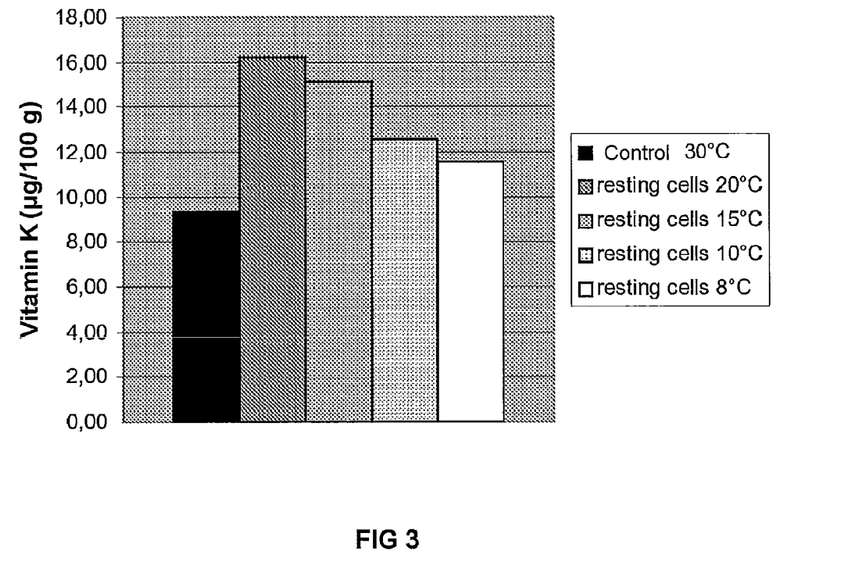
FIG. 3: Histogram presenting vitamin K2 production by resting-cell cultures at various temperatures. Control: culture under standard growth conditions.

As shown in FIG. 3, the drop in temperature did not have a positive impact on vitamin K2 production. On the other hand, cultivating the bacteria in resting cells multiplied production by a factor of about 2: 20 µg/100 g compared to 10 µg/100 g for standard fermentation with growth.

B-III—Influence of Implementing Pre-Culture in Respiration Conditions

Vitamin K2 takes part in the respiratory chain. *L. lactis* is capable of respiration but this respiration only intervenes at the end of fermentation, i.e., when metabolic flux slows. This property can be compared to that observed in vitamin K2 production kinetics.

It is important to note that manufacturing a food product entirely under respiration conditions appears difficult to achieve on an industrial scale. Indeed, problems of aeration, agitation, foaming, etc., would be difficult to overcome without reviewing typical equipment and manufacturing processes, which would require very large investments and would generate additional production expenditures unacceptable to the food industry.

On the other hand, if the need arises, pre-culture could be carried out under respiration conditions without posing too many difficulties for manufacturers.

The Inventors thus studied the impact of pre-culture in respiration conditions on vitamin K2 production by lactic acid bacteria.

To this end, pre-cultures were produced on M17 Lac medium supplemented with 20 µl/ml of a 0.5 mg/ml haemin solution in 0.1 M soda. Inoculation was carried out at 1% and incubation temperature was 30° C. Aeration was ensured by simple agitation.

First, these pre-cultures made it possible to inoculate whole milk at 1%, which is traditional fermentation. Under these conditions, no positive impact on vitamin K2 production was observed (data not shown).

These pre-cultures were then used to carry out fermentations in resting-cell conditions. The pre-cultures were produced as previously described and maintained overnight. Then, 50 ml samples were centrifuged at 6000 g for 5 minutes. The supernatant was removed and replaced by whole milk. The milk was then incubated at 30° C. for 24 hours. The samples were frozen at −80° C. for subsequent analysis.

Figure 4:
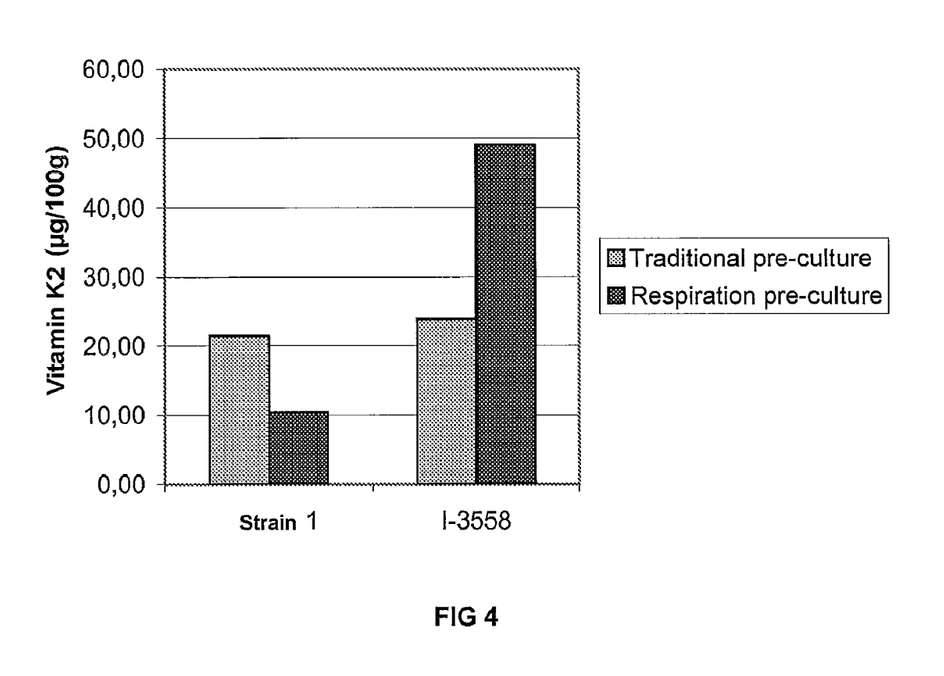
FIG. 4: Histogram presenting the influence of pre-culture conditions on vitamin K2 production according to strain.

As shown in FIG. 4, the behaviour observed was different according to the strain. Pre-culture in respiration conditions did not have an impact on vitamin K2 production by *L. lactis* subsp. *cremoris* natural strain no. 1. On the other hand, it increased by a factor of 2 vitamin K2 production by natural variant I-3558.

The approach using pre-culture in respiration conditions thus appeared advantageous for certain strains at least.

However, in practise, it is important to have available not fresh pre-cultures but frozen ferments. Moreover, in order to carry out fermentations in resting-cell conditions, it is advisable to have concentrated ferments.

B-IV—Supplementary Results Concerning the Stimulating Effect of Respiration on Vitamin K2 Production These results are to be placed in relation to section A-III above.

As indicated in paragraph A-III-2 above, the culture of selected natural variant I-3626 in the presence of structural analogues of aromatic amino acids was used to inoculate 50 ml of M17 Lac medium (1% inoculation rate) supplemented with 1 ml of haemin solution (500 mg/l). The same culture was used to inoculate a medium not containing haemin but placed under agitation. A last type of culture was produced. M17 Lac medium was inoculated and placed at 30° C. without agitation. The cultures were placed overnight at 30° C. under agitation (250 rpm). These cultures were then centrifuged for 5 minutes at 6000 g. The supernatant was removed and replaced by 50 ml of whole milk. After 24 hours, the fermented milk was placed at −80° C. while awaiting analysis of vitamin K2.

Table III below gives the results of vitamin K2 production by natural variant I-3626 according to the conditions of implementation. The quantity of vitamin K2 is expressed in µg Equivalent MK-4 per 100 g of fermented milk.

TABLE III

| Pre-culture type | Without agitation Without haemin | With agitation With haemin |
|---|---|---|
| Vitamin K2 | 0.77 | 25.77 |

These results show that respiration (presence of haemin under agitation) has a very large impact on vitamin K2 production. Under these conditions, vitamin production is increased by a factor of 5. The master strain produced 21.5 µg/100 g after pre-culture without respiration (data not shown). When pre-culture was carried out in respiration conditions, production dropped to 10.3 µg/100 g (data not shown). Thus, for the master strain, pre-culture in respiration conditions had a negative effect on vitamin K2 production.

B-V—Influence of Inoculation Dose, Final Bacterial Population, and Milk pH

Under the resting-cell conditions previously described for pre-culture in respiration, the initial bacterial population increases to about $10^{10}$ CFU/ml.

Since this inoculation dose is not easily applicable in the context of an industrial process, the Inventors studied the precise influence of the initial quantity of cells on vitamin K2 production during the milk fermentation phase.

In addition, since the quantity of cells is greater in pre-culture in respiration conditions than in traditional pre-culture, the Inventors sought to determine if the increase in production observed for pre-cultures in respiration conditions was due to a simple increase in the inoculation dose, or to a specific contribution of the respiration process.

The Inventors also sought to determine if the final bacterial population, after the resting-cell phase, played a determining role in the quantity of vitamin K2 obtained. Knowing that there is a certain bacterial mortality due to the reduction in pH during fermentation, amongst other causes, the Inventors studied the impact of the use of buffered milk on the level of vitamin K2 production.

In order to answer these various questions, tests were conducted in resting-cell conditions, in traditional or buffered milk, with inoculation doses ranging from about $10^6$ CFU/ml to about $10^{10}$ CFU/ml from traditional pre-cultures or those in respiration.

Pre-cultures of strain I-3558 were carried out on M17 Lac medium at 30° C. For experiments in respiration conditions, the medium was supplemented with 20 μl/ml of 0.5 mg/ml haemin solution (in 0.1 M soda) and the pre-culture was agitated during incubation overnight. Various volumes of these pre-cultures (see Table IV below) were then centrifuged at 10,000 g for 10 minutes.

TABLE IV

| Inoculation | Pre-culture volume (R+) | Pre-culture volume (R−) |
|---|---|---|
| 100% | 40 ml | 160 ml |
| 75% | 30 ml | 120 ml |
| 50% | 20 ml | 80 ml |
| 30% | 12 ml | 48 ml |
| 20% | 8 ml | 32 ml |
| 10% | 4 ml | 16 ml |
| 5% | 2 ml | 8 ml |
| 1% | 0.4 ml | 1.6 ml |
| 0.01% | 0.04 ml | 0.16 ml |

The supernatant was removed and either replaced by 40 ml of traditional whole milk (pre-cultures R+ and R−), or supplemented with β-glycerophosphate at a final concentration of 0.075 M (pre-culture R+ only). The samples were then incubated at 30° C. for 24 hours. An aliquot was taken for purposes of enumeration and then the samples were frozen at −80° C. for subsequent analysis. Results of analyses and enumerations carried out before and after the resting-cell phase are indicated in Table V below. This table provides the results of the analysis of vitamin K2 and the enumerations carried out before (T0) and after the resting-cell phase (Tf) from traditional pre-cultures or those in respiration.

TABLE V

| Dose | T0 R− | Tf R− | VitK R− | T0 R+ | Tf R+ | VitK R+ | T0 R+ TP | Tf R+ TP | VitK R+ TP |
|---|---|---|---|---|---|---|---|---|---|
| 100% | 1.08E+10 | 9.70E+09 | 44.47 | 3.40E+09 | 2.65E+09 | | 3.40E+09 | 5.30E+09 | 35.9 |
| 75% | 8.10E+09 | 4.30E+09 | 29.01 | 2.55E+09 | 2.40E+09 | | 2.55E+09 | 5.80E+09 | |
| 50% | 5.40E+09 | 4.15E+09 | 18.58 | 1.70E+09 | 1.64E+09 | 19.82 | 1.70E+09 | 6.40E+09 | 26.7 |
| 30% | 3.24E+09 | 4.25E+09 | 13.72 | 1.02E+09 | 1.20E+09 | 16.75 | 1.02E+09 | 7.70E+09 | |
| 20% | 2.16E+09 | 2.10E+09 | 9.13 | 6.80E+08 | 1.60E+09 | 14.09 | 6.80E+08 | 6.40E+09 | 18.55 |
| 10% | 1.08E+09 | 2.10E+09 | | 3.40E+08 | 1.17E+09 | | 3.40E+08 | 4.60E+09 | |
| 5% | 5.40E+08 | 1.10E+09 | 6.4 | 1.70E+08 | 1.29E+09 | 9.41 | 1.70E+08 | 3.60E+09 | 13.666 |
| 1% | 1.08E+08 | 2.15E+09 | 6.88 | 3.40E+07 | 1.25E+09 | 6.35 | 3.40E+07 | 4.20E+09 | |
| 0.1% | 1.08E+07 | 1.50E+09 | 6.26 | 3.40E+06 | 1.27E+09 | 6.19 | 3.40E+06 | 4.80E+09 | |

R− = traditional pre-culture
R+ = pre-culture in respiration
TP = fermentation in milk buffered with β-glycerophosphate
T0 = initial bacterial population in CFU/ml of culture
Tf = final bacterial population in CFU/ml of culture
VitK = concentration of vitamin K2 in μg Equivalent MK-4/100 g of product.

Figure 5:
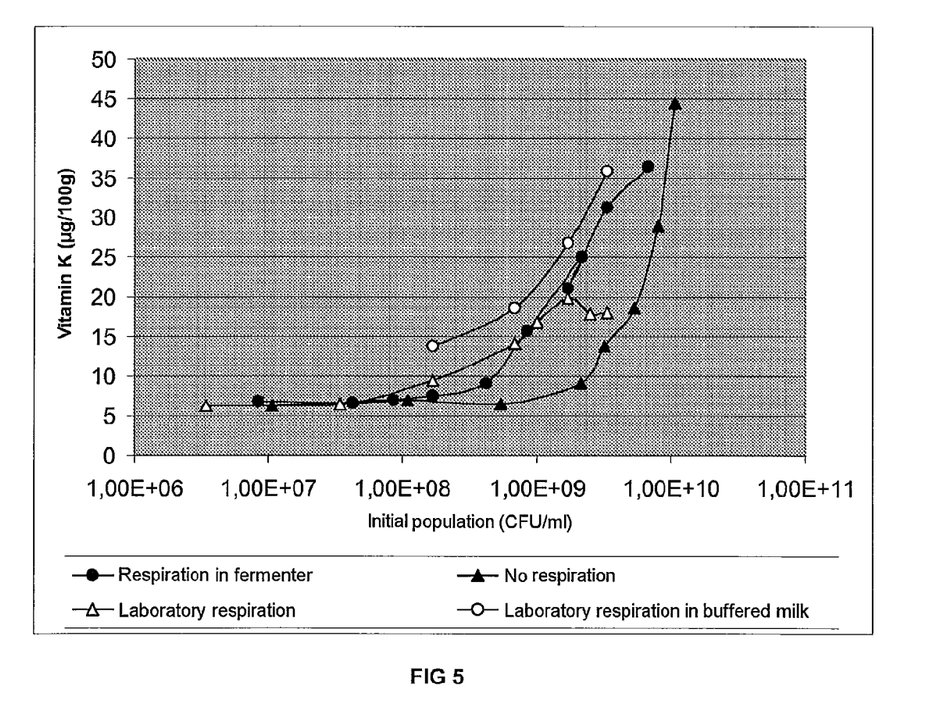
FIG. 5: Graph illustrating the influence of the initial bacterial population of natural variant I-3558 on vitamin K2 production during the resting-cell phase, conducted using conventional milk or buffered milk. "Without respiration": traditional pre-culture and then culture in resting-cell conditions in whole milk. "Laboratory respiration": pre-culture under respiration conditions conducted in a test tube and then culture in resting-cell conditions in whole milk. "Laboratory respiration in buffered milk": pre-culture under respiration conditions and then culture in resting-cell conditions in milk buffered with β-glycerophosphate. "Respiration in fermenter": pre-culture under respiration conditions conducted in a fermenter followed by culture in resting-cell conditions in traditional milk.
Figure 6:
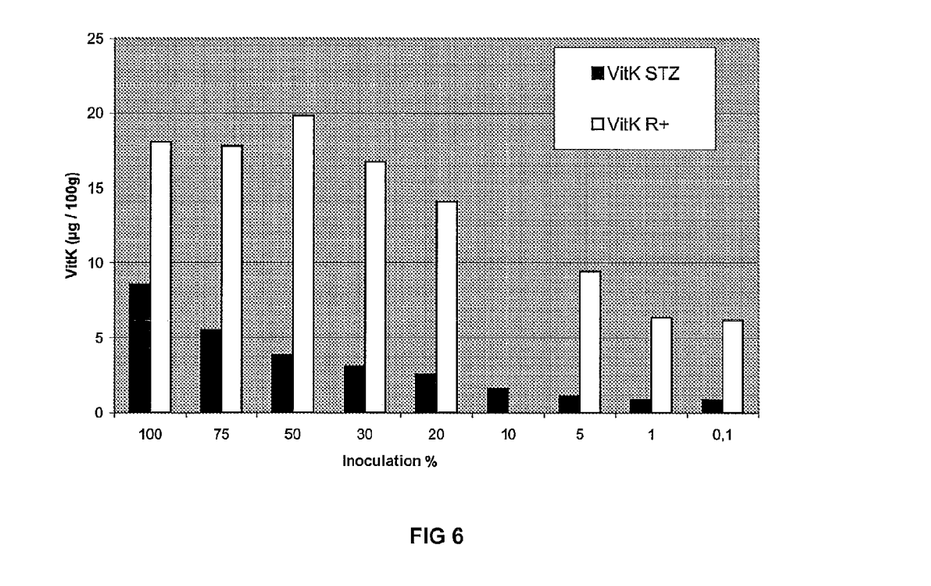
FIG. 6: Histogram presenting the influence of the bacterial viability of natural variant I-3558 on vitamin K2 production during the resting-cell phase. VitK STZ: pre-culture in respiration conditions treated with streptozotocin and then culture in resting-cell conditions in whole milk supplemented with erythromycin. VitK R+: pre-culture under respiration conditions conducted in a test tube and then culture in resting-cell conditions in whole milk.

The results obtained are represented in FIG. 5. Also represented, for illustration, are the results obtained with a pre-culture in respiration conditions, carried out in a fermenter followed by a resting-cell phase in traditional milk ("respiration in fermenter" curve). The results are comparable with those obtained with pre-cultures in test tubes ("laboratory respiration" curve).

The results obtained (Table V and FIG. 5) indicated that:

Vitamin K2 content depended on inoculation dose;

The slope of the curve was greater for pre-culture in respiration conditions than for traditional pre-culture. Thus, for a given bacterial population, vitamin K2 production was greater when pre-culture was carried out in respiration conditions. The benefit observed in respiration conditions thus seemed due to a specific contribution of the respiration process rather than to a simple increase in inoculation dose, which confirmed the advantage of this approach;

Vitamin K2 production was greater when the resting-cell phase was carried out in buffered milk. This could be due either to better survival of bacteria in this medium, since for the same initial population the final population was 2 to 6 times higher in buffered milk compared to traditional milk (see Table V), or a better "extraction" of vitamin K2 in buffered milk.

REFERENCES

Bolotin et al., 2001. *Genome Research* 11, 731-753
Duwat et al., 2001. *J. Bacteriol.* 183(15), 4509-16

Morishita et al., 1999. *J. Dairy Sci.* 82, 1897-1903
Parker et al., 2003. *Journal of Food Science* 68(7), 2325-2330
Vido et al., 2005. *J. Bact.* 187, 601-10
Hart J P, et al., [letter]. *Lancet.* 1984; 2:283
Hart J P, et al., *J Clin Endocrinol Metab.* 1985; 60:1268-9
Hauschka P V, et al., *Physiol Rev.* 1989; 69:990-1047
Ducy P, et al., *Nature.* 1996; 382:448-52
Väänänen H K, et al., *Calcif Tissue Int.* 1999; 64:S79
Ronden J E, et al., *Biochim Biophys Acta.* 1998; 1379:16-22
Knapen M H, et al., *Ann Intern Med.* 1989 Dec. 15; 111 (12):1001-5
Szulc P, et al., *J Clin Invest.* 1993 April; 91 (4):1769-74
Booth S L, et al., *Am J Clin Nutr.* 2000; 71:1201-8
Shiraki M, et al., *J Bone Miner Res.* 2000; 15:515-21
Braam L A J L M, et al., *Calcif Tissue Int.* 2003 July; 73 (1):21-6
Hirano J and Ishii Y. *J Orthop Sci.* 2002; 7:364-369.
Cocaign-Bousquet M, et al., *Journal of Applied Bacteriology* 1995; 79, 108-116

The invention claimed is:

1. A method to increase the quantity of vitamin K2 obtained by cultivating at least one strain of lactic acid bacterium that produces vitamin K2, wherein said strain is cultured in resting-cell conditions, said method comprising at least:
   a) pre-culturing said strain under respiration conditions, in a suitable pre-culture medium containing at least one porphyrin at a final concentration of at least about 0.5 μg/ml;
   b) innoculating a suitable culture medium containing at least about 5% fat with a quantity of living bacterial cells of said strain ranging from about $10^8$ CFU/ml to about $10^{11}$ CFU/ml; and,
   c) fermenting the medium thus inoculated for a period ranging from about 4 hours to about 48 hours, at a temperature ranging from about 4° C. to about 50° C., in such a way that, at the end of step c), the quantity of vitamin K2 produced by the resting-cell culture is higher, by a factor at least equal to about 1.2, than that obtained by cultivating said strain under standard fermentation conditions.

2. The method according to claim 1, wherein said suitable culture medium is plain milk or milk whose buffering capacity has been increased.

3. The method according to claim 1, wherein the incubation of said pre-culturing step is performed at a temperature ranging from about 4° C. to about 40° C.

4. The method according to claim 1, wherein respiration in said pre-culturing step is obtained through an oxygenation carried out by agitation or aeration.

5. The method according to claim 1, wherein said pre-culturing step is maintained for at least about 8 hours.

6. The method according to claim 1, wherein said strain of lactic acid bacterium that produces vitamin K2 is selected from the genera *Lactococcus, Leuconostoc, Enterococcus*, and *Propionibacterium*.

7. The method according to claim 6, wherein said strain of lactic acid bacterium is selected from the group consisting of the species *Lactococcus lactis, Leuconostoc lactis, Leuconostoc pseudomesenteroides, Leuconostoc mesenteroides, Leuconostoc dextranicum, Enterococcus faecium*, and *Propionibacterium* sp.

8. The method according to claim 7, wherein said strain of lactic acid bacterium is selected from the group consisting of the natural variants of *Lactococcus lactis* subsp. *cremoris* that produce vitamin K2:
   I-3557 filed with France's Collection Nationale de Culture des Microorganismes (CNCM, Pasteur Institute, 25, rue du Docteur Roux, 75724 Paris cedex 15, France) on Jan. 20, 2006,
   I-3558 filed with the CNCM (Pasteur Institute, 25, rue du Docteur Roux, 75724 Paris cedex 15, France) on Jan. 20, 2006, and,
   I-3626 filed with the CNCM (Pasteur Institute, 25, rue du Docteur Roux, 75724 Paris cedex 15, France) on Jun. 19, 2006.

9. A method for producing vitamin K2, comprising at least:
   a) implementation of the method according to claim 1; and,
   b) recovery of the vitamin K2 thus produced.

10. A method for preparing a food product enriched in vitamin K2, comprising at least:
   a) culturing at least one strain of lactic acid bacterium that produces vitamin K2 under resting-cell conditions in accordance with the method of claim 1;
   b) adding the biomass obtained from the culture in step a) to said food product or to an intermediate preparation of same; and,
   c) obtaining said food product enriched in vitamin K2.

* * * * *